United States Patent
Park et al.

(10) Patent No.: US 9,943,276 B2
(45) Date of Patent: Apr. 17, 2018

(54) X-RAY DETECTION TABLE, X-RAY IMAGING APPARATUS, AND CONTROL METHOD OF X-RAY IMAGING APPARATUS

(71) Applicant: SAMSUNG ELECTRONICS CO., LTD., Suwon-si, Gyeonggi-do (KR)

(72) Inventors: Tae Wook Park, Seoul (KR); Woo Sup Han, Yongin-si (KR)

(73) Assignee: SAMSUNG ELECTRONICS CO., LTD., Suwon-Si (KR)

(*) Notice: Subject to any disclaimer, the term of this patent is extended or adjusted under 35 U.S.C. 154(b) by 186 days.

(21) Appl. No.: 14/017,792

(22) Filed: Sep. 4, 2013

(65) Prior Publication Data

US 2014/0072101 A1    Mar. 13, 2014

(30) Foreign Application Priority Data

Sep. 7, 2012  (KR) .................. 10-2012-0099444

(51) Int. Cl.
*A61B 6/00* (2006.01)

(52) U.S. Cl.
CPC .............. *A61B 6/467* (2013.01); *A61B 6/461* (2013.01); *A61B 6/462* (2013.01)

(58) Field of Classification Search
CPC .......... A61B 6/461; A61B 6/462; A61B 6/467
See application file for complete search history.

(56) References Cited

U.S. PATENT DOCUMENTS

| | | | |
|---|---|---|---|
| 6,785,578 B2 | 8/2004 | Johnson et al. | |
| 7,602,882 B2 | 10/2009 | Dörre | |
| 7,664,557 B2 * | 2/2010 | Danzer | A61B 6/548 607/60 |
| 8,850,640 B2 * | 10/2014 | Buettner | A61B 5/7475 5/601 |
| 2001/0024487 A1 | 9/2001 | Akutsu et al. | |
| 2003/0069653 A1 | 4/2003 | Johnson et al. | |
| 2008/0069309 A1 | 3/2008 | Dorre | |
| 2012/0257724 A1 * | 10/2012 | Nakamura | A61B 6/0414 378/189 |

FOREIGN PATENT DOCUMENTS

| | | |
|---|---|---|
| CN | 1984606 A | 6/2007 |
| CN | 102551743 A | 7/2012 |
| CN | 102655811 A | 9/2012 |

OTHER PUBLICATIONS

European Search Report dated Nov. 4, 2013 from European Patent Application No. 13183077.0, 6 pages.

(Continued)

*Primary Examiner* — Dani Fox

(74) *Attorney, Agent, or Firm* — Staas & Halsey LLP

(57) ABSTRACT

An X-ray detection module, an X-ray imaging apparatus, and a control method of an X-ray imaging apparatus include a movable X-ray irradiation module to irradiate an object with X-rays, an X-ray detection module including a movable X-ray detector to detect X-rays from the X-ray irradiation module, and a touch sensor device installed to the X-ray detection module and located in a movement direction of the X-ray detector to sense touch. If the touch sensor device senses a touch, at least one of the X-ray irradiation module and the X-ray detector is moved to a position where the touch is sensed.

15 Claims, 16 Drawing Sheets

(56) References Cited

OTHER PUBLICATIONS

European Office Action dated Jan. 3, 2017 from European Patent Application No. 13183077.0, 94 pages.
Chinese Office Action dated Jan. 26, 2017 in corresponding Chinese Patent Application No. 201310406471.8.
Chinese Office Action dated Jun. 29, 2017 from Chinese Patent Application No. 201310406471.8, 8 pages.

* cited by examiner

POSITION AFTER MOVEMENT($\ell 2$)

X-RAY DETECTION TABLE, X-RAY IMAGING APPARATUS, AND CONTROL METHOD OF X-RAY IMAGING APPARATUS

CROSS-REFERENCE TO RELATED APPLICATIONS

This application claims the priority benefit of Korean Patent Application No. 10-2012-0099444, filed on Sep. 7, 2012 in the Korean Intellectual Property Office, the disclosure of which is incorporated herein by reference.

BACKGROUND

1. Field

Embodiments disclosed herein relate to an X-ray detection table, an X-ray imaging apparatus, and a control method of an X-ray imaging apparatus.

2. Description of the Related Art

An X-ray imaging apparatus may refer to an image apparatus that acquires an image of internal material, tissues, or structures of an object, such as a human body, animal, and other various things. The image may be acquired by irradiating the object with X-rays, detecting the irradiated X-rays, and generating an X-ray image based on the detected result to display the X-ray image on a display device.

X-ray imaging using the X-ray imaging apparatus may enable easy observation of the internal material or structure of the object without destruction of the object, and is thus used in a wide variety of fields including medicine, etc.

The X-ray imaging apparatus includes an X-ray irradiation module that irradiates an object with X-rays, and an X-ray detection module that detects the X-rays irradiated from the X-ray irradiation module to generate an X-ray image.

The X-ray irradiation module applies a predetermined voltage to an X-ray tube to accelerate electrons in the X-ray tube based on the applied voltage, and irradiates an object with X-rays generated when the accelerated electrons are rapidly reduced in speed upon collision with an anode.

The X-ray detection module receives X-rays, directed to the object and passed through the object, or X-rays directed to an external region of the object, through an X-ray detection panel, and converts the received X-rays into electric signals. Thereafter, the X-ray detection module reads out the electric signals to generate an X-ray image. More specifically, to convert X-rays into electric signals, the X-ray detection panel includes a scintillator to receive X-rays and output photons, a photodiode to receive the photons output from the scintillator and convert the photons into electric signals, and a storage unit to store the electric signals converted by the photodiode, the storage unit being, for example, a storage capacitor.

The object is located at an upper end or a front end of the X-ray detection module. For example, in the case of the X-ray detection module in the form of a table, the object is located at the upper end of the X-ray detection module.

Examples of the above-described X-ray imaging apparatus include a general X-ray imaging apparatus, a special area dedicated imaging apparatus, and a Computed Tomography (CT) or Full Field Digital Mammography (FFDM) apparatus.

SUMMARY

It is an aspect of the present invention to provide an X-ray detection module which may easily and accurately move at least one of an X-ray irradiation module and an X-ray detector that detects X-rays from the X-ray irradiation module to a position where a user desires, i.e. a position where the user desires to perform X-ray imaging, thereby enhancing use convenience, an X-ray imaging apparatus, and a control method of the X-ray imaging apparatus.

Additional aspects of the invention will be set forth in part in the description which follows and, in part, will be apparent from the description, or may be learned by practice of the invention.

In accordance with one aspect of the present invention, a X-ray detection module includes a movable X-ray detector to detect X-rays, and a touch sensor device arranged in a movement direction of the X-ray detector to sense a touch, wherein at least one of an X-ray irradiation module and the X-ray detector is moved to a position where the touch is sensed if the touch sensor device senses the touch.

The touch sensor device may be located near both boundaries of the X-ray detector in the movement direction of the X-ray detector. Only a selected partial region of the touch sensor device may sense the touch, or the at least one of the X-ray irradiation module and the X-ray detector may be moved only to the selected partial region.

The X-ray detector and/or X-ray irradiation module may be moved while the touch sensor device senses the touch. The X-ray irradiation module and the X-ray detector may stop moving in response to the touch sensor device failing to continue sensing the touch.

In accordance with another aspect of the present invention, an X-ray detection module includes an X-ray detector to detect X-rays from a movable X-ray irradiation module, and a touch sensor device located on at least one side of the X-ray detector to sense a touch, wherein the X-ray irradiation module is moved to a position where the touch is sensed if the touch sensor device senses the touch. The X-ray detector may be disposed in a fixed position.

In accordance with another aspect of the present invention, an X-ray imaging apparatus includes a movable X-ray irradiation module to irradiate an object with X-rays, an X-ray detection module including a movable X-ray detector to detect X-rays from the X-ray irradiation module, and a touch sensor device installed to the X-ray detection module and located in a movement direction of the X-ray detector to sense a touch, wherein at least one of the X-ray irradiation module and the X-ray detector is moved to a position where the touch is sensed if the touch sensor device senses the touch.

The touch sensor device may be located near both boundaries of the X-ray detector in the movement direction of the X-ray detector.

The least one of the X-ray irradiation module and the X-ray detector may be moved while the touch sensor device senses the touch.

Only a selected partial region of the touch sensor device may sense the touch, or the at least one of the X-ray irradiation module and the X-ray detector may be moved only to the selected partial region. In this case, the partial region of the touch sensor device may be selected in response to a selection instruction for the partial region.

In accordance with another aspect of the present invention, an X-ray imaging apparatus includes a movable X-ray irradiation module to irradiate an object with X-rays, an X-ray detection module including a movable X-ray detector to detect X-rays from the X-ray irradiation module, and a touch sensor device installed to the X-ray detection module and located on at least one side of the X-ray detector to sense touch, wherein the X-ray irradiation module is moved to a position where touch is sensed if the touch sensor device senses the touch.

In accordance with another aspect of the present invention, an X-ray imaging apparatus includes a movable X-ray irradiation module to irradiate an object with X-rays, an X-ray detection module including a movable X-ray detector to detect X-rays from the X-ray irradiation module, a touch sensor device installed to the X-ray detection module and located in a movement direction of the X-ray detector to sense a touch, and a controller that acquires a coordinate value of a post-movement position of at least one of the X-ray irradiation module and the X-ray detector based on a touch position sensed by the touch sensor device, and moves the at least one of the X-ray irradiation module and the X-ray detector based on the coordinate value of the post-movement position.

In accordance with another aspect of the present invention, a control method of an X-ray imaging apparatus includes sensing a touch by a touch sensor device, acquiring positional information on a movement position of at least one of an X-ray irradiation module and an X-ray detector based on a touch position sensed by the touch sensor device, and moving the at least one of the X-ray irradiation module and the X-ray detector based on the positional information.

The sensing of touch by the touch sensor device may include sensing a touch by at least one touch sensing device of a plurality of touch sensing devices arranged near both boundaries of the X-ray detector in the movement direction of the X-ray detector.

The movement of the at least one of the X-ray irradiation module and the X-ray detector may include moving at least one of the X-ray irradiation module and the X-ray detector during the sensing of the touch.

In accordance with another aspect of the present invention, a control method of an X-ray imaging apparatus includes selecting and activating a partial region of the touch sensor device, sensing a touch on the partial region of the touch sensor device, acquiring positional information on a movement position of at least one of the X-ray irradiation module and the X-ray detector based on a touch position sensed by the partial region of the touch sensor device, and moving the at least one of the X-ray irradiation module and the X-ray detector based on the positional information.

The sensing of touch by the touch sensor device includes sensing a touch by at least one touch sensing device of a plurality of touch sensing devices arranged near both boundaries of the X-ray detector in the movement direction of the X-ray detector.

The movement of the at least one of the X-ray irradiation module and the X-ray detector may include moving at least one of the X-ray irradiation module and the X-ray detector during the sensing of the touch.

In accordance with a further aspect of the present invention, a control method of an X-ray imaging apparatus includes sensing a touch by the touch sensor device, acquiring positional information on a movement position of the X-ray irradiation module based on a touch position on the touch sensor device, and moving the X-ray irradiation module based on the positional information.

In accordance with a further aspect of the present invention, an X-ray imaging apparatus may include an X-ray irradiation module to irradiate X-rays; a X-ray detection module including an X-ray detector to detect X-rays from the X-ray irradiation module, a first plurality of touch sensor devices to sense a touch and installed along a first side of the X-ray detection module, and a controller to determine a first coordinate value corresponding to a position of a first sensed touch at one of the first plurality of touch sensor devices and to calculate a post-movement coordinate value to which at least one of the X-ray irradiation module and the X-ray detector move.

The X-ray imaging apparatus may further include a second plurality of touch sensor devices to sense a touch, installed along a second side of the X-ray detection module, wherein the first side and second side are perpendicular to one another.

The X-ray detector may move in a direction parallel to the first side when a touch is sensed at one of the first plurality of touch sensor devices, and may move in a direction parallel to the second side when a touch is sensed at one of the second plurality of touch sensor devices. Each of the first plurality of touch sensor devices may be selectively activated or deactivated according to a user input.

The first coordinate value of the first sensed touch may be substantially equal to the post-movement coordinate value, or the first coordinate value of the first sensed touch may be corrected and the post-movement coordinate value offset from the first coordinate value by a predetermined amount.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
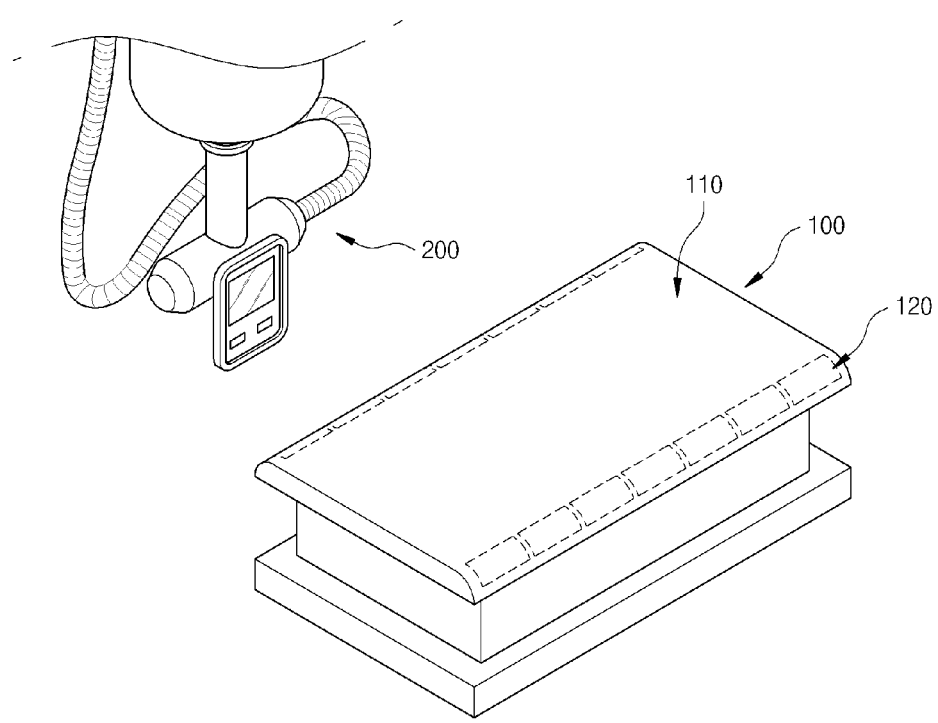
FIG. 1 is a perspective view illustrating an embodiment of an X-ray imaging apparatus.

Reference will now be made in detail to the embodiments of the present invention, examples of which are illustrated in the accompanying drawings, wherein like reference numerals refer to like elements throughout.

To explain the embodiments of the present invention via FIGS. 1 to 15, one embodiment of an X-ray imaging apparatus and an X-ray detection module will first be described with reference to FIGS. 1 to 11. Subsequently, the embodiments of a control method of the X-ray imaging apparatus will be described with reference to FIGS. 12 to 15.

Figure 2:
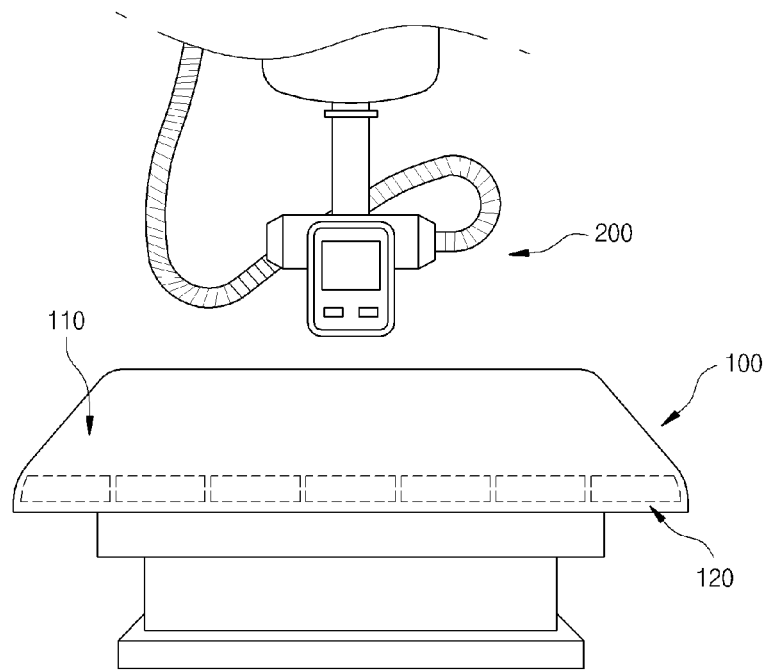
FIG. 2 is a front view of the embodiment of the X-ray imaging apparatus.

FIGS. 1 and 2 are respectively a perspective view and a front view illustrating an embodiment of the X-ray imaging apparatus.

As illustrated in FIG. 1, according to the embodiment of the X-ray imaging apparatus, the X-ray imaging apparatus may include an X-ray detection module 100 and an X-ray irradiation module 200.

According to the embodiment of the X-ray imaging apparatus, the X-ray imaging apparatus may include the X-ray detection module 100 which be disposed or integrated with a table and the X-ray irradiation module 200 arranged above the X-ray detection module 100, as illustrated in FIGS. 1 and 2. The table may be mobile or fixed, and may be adjustable in various directions. In this case, the X-ray irradiation module 200, for example, may direct X-rays toward the ground to allow the X-ray detection module 100 to detect the X-rays. That is, the X-ray irradiation module 200 may direct X-rays in a substantially downward vertical direction toward an object to be X-rayed which may be disposed on the table or X-ray detection module 100.

According to another embodiment of the X-ray imaging apparatus, the X-ray imaging apparatus may include an X-ray irradiation module 200 configured to direct X-rays in a direction substantially horizontal to the ground toward an object, for example, a human body, and an X-ray detection module 100 to receive X-rays from the X-ray irradiation module 200 in the direction substantially horizontal to the ground. In this case, the X-ray detection module 100 may be configured such that an X-ray detector (130 in FIG. 4) that detects X-rays is positioned in an upright vertical direction which is substantially perpendicular to the ground. However, the X-ray irradiation module 200 and X-ray detection module 100 may be physically arranged with respect to one another in other orientations, and the above-described embodiments are merely non-limiting examples. Essentially, the X-ray irradiation module 200 and X-ray detection module 100 may be arranged in any configuration so long as the X-ray irradiation module 200 is capable of directing X-rays toward an object, and the X-ray detection module is capable of detecting or receiving the X-rays which pass through the object.

According to a further embodiment of the X-ray imaging apparatus, the X-ray imaging apparatus may correspond to a full field digital mammography (FFDM) apparatus. Generally, a FFDM apparatus may be used to obtain an X-ray image of a patient's breast. Generally, the patient may be standing. In this case, the X-ray irradiation module 200 may be located at the top of the FFDM apparatus, and the X-ray detection module 100 may be located at the middle of the FFDM apparatus. Generally, to obtain a higher quality image, the patient's breast may be compressed using a compressor device (e.g., two plates which compress the breast disposed in between) before obtaining the X-ray image. The X-ray detection module 100 may be provided at an upper end thereof with a compressor that compresses the breast of an object placed over the X-ray detection module 100.

According to the embodiment of the present invention, the X-ray detection module 100 includes the X-ray detector (130 in FIG. 4) that receives X-rays from the X-ray irradiation module 200 and changes the received X-rays into an electric signal, thereby enabling generation of an X-ray image corresponding to the received X-rays.

The X-ray detection module 100, as illustrated in FIGS. 1 and 2, may include, for example, a support member 110 in the form of a top plate. The support member 110 supports, by an upper surface thereof, an object to be X-rayed, for example, a part or all of an object (e.g., a part or all of a patient's body), thereby allowing the object to be irradiated with X-rays by the X-ray irradiation module 200.

If the X-ray detection module 100 takes the form of (or integrated with) a table, the X-ray detector 130 may be arranged at a lower end of the support member 110. According to another embodiment of the present invention, if the X-ray detection module 100 is vertically upright, the X-ray detector 130 may be installed to a rear surface of the support member 110. That is, the X-ray detector 130 may be disposed beneath a first side of the support member 110 in a case in which the X-ray detection module 100 is horizontally oriented, while the X-ray irradiation module 200 may be disposed above a second side of the support member 110, the second side of the support member 110 being opposite to the first side of the support member 110. Likewise, the X-ray detector 130 may be disposed to the rear of a first side of the support member 110 in a case in which the X-ray detection module 100 is vertically oriented, while the X-ray irradiation module 200 may be disposed in front of a second side of the support member 110, the second side of the support member 110 being opposite to the first side of the support member 110.

The above-described support member 110 may be formed of an X-ray permeable material to allow transmission of X-rays having passed through the object to be directed to the X-ray detector 130. As such, the X-rays may reach the X-ray detector 130 located at the lower end or the rear surface of the support member 110. Consequently, the X-ray detector 130 may receive the X-rays having passed through the object.

The X-ray detection module 100, as illustrated in FIGS. 1 and 2, may include a touch sensor device 120 to sense an external touch.

The touch sensor device 120, as illustrated in FIGS. 1 and 2, may include at least one touch sensor unit to sense an external touch.

The at least one touch sensor unit may have a sufficient volume to sense an external touch, for example, contact of a user's finger or a touch pen, and may generate an electric signal based on the sensed contact to transmit the electric signal to other elements, for example, a controller.

The user may control the X-ray imaging apparatus by, for example, performing a touch action on the touch sensor device 120. More particularly, the user may control movement of the X-ray detector 130 of the X-ray detection module 100 or the X-ray irradiation module 200 included in the X-ray imaging apparatus to a predetermined position.

The touch sensor unit may sense an external touch and a touch position via various methods including capacitive overlay, resistive overlay, surface ultrasonic wave, and infrared beam methods.

For example, the capacitive overlay touch sensor unit may sense a touch action or a touch position by recognizing a change in a waveform if a high-frequency generated by applying voltage to each corner or each side of the touch sensor unit is changed in waveform based on a contact of the finger.

Figure 3:
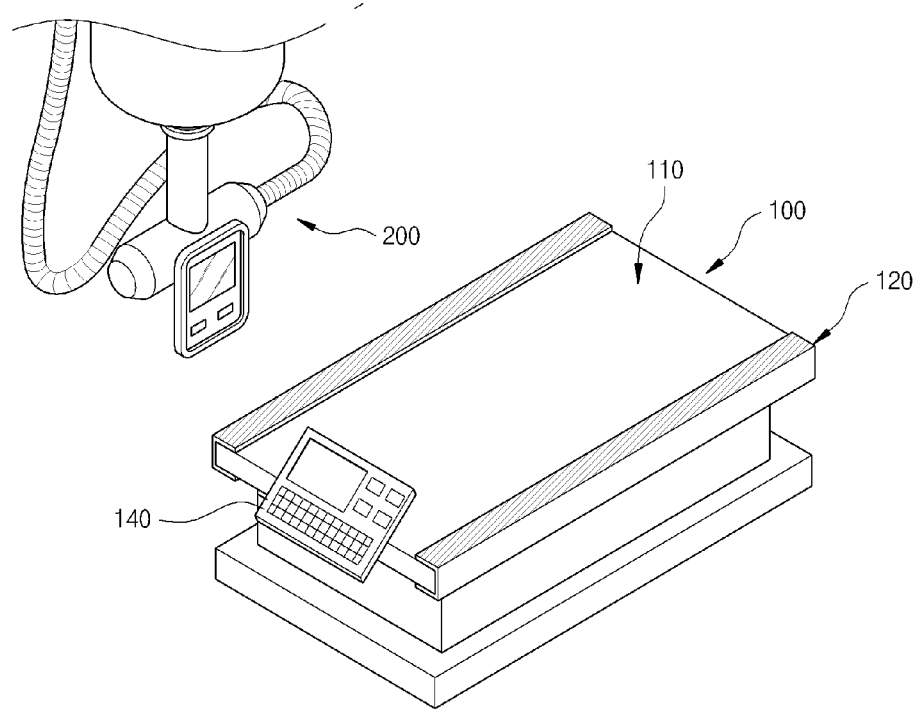
FIG. 3 is a perspective view illustrating another embodiment of the X-ray imaging apparatus.

The touch sensor device 120 may be located aside the above-described X-ray detector 130. As illustrated in FIGS. 1 to 3, the touch sensor device 120 may be arranged in a line on at least one side of the support member 110. That is, the touch sensor device 120 may be arranged along a longitudinal direction of the X-ray detection module 100. Further, the touch sensor device 120 may be disposed on a portion of at least one side of the support member 110.

According to an embodiment of the present invention, only a selected partial region of the touch sensor device 120 may sense a touch. For example, only some of the plurality of touch sensor units 120a to 120g (FIG. 4) of the touch sensor device 120 (for example, touch sensor units 120a, 120c, 120e and 120g) may be activated to sense a user touch action.

For example, if the touch sensor units 120a to 120g are arranged in plural lines on at least one lateral side of the support member 110, a touch action may be generated via an unintentional movement of the object, for example, the patient. In this case, the touch sensor units in the line close to the patient may be inactivated and the touch sensor units in the line distant from the patient may be activated, which may prevent malfunction due to movement of the patient. That is, the touch sensor units 120a to 120g may be arranged side by side along a longitudinal direction of the X-ray detection module 100, and may be selectively activated or deactivated according to a user input.

For example, only some of the touch sensor units may be activated based on an X-ray imaging position, i.e. the patient's position, or based on the likelihood of an accidental-touch due to movement of the patient.

According to an embodiment, a partial region of the touch sensor device 120 may be selected upon receiving a predetermined selection instruction via a separate input unit (for example, via input unit 140 in FIG. 3) and the selected partial region may be activated or inactivated. For example, a user may select a plurality of partial regions at one time via the input unit 140 and activate and/or deactivate those partial regions. Alternatively, a user may only be able to select one partial region at a time via the input unit 140, to activate or deactivate the partial region.

According to another embodiment, the touch sensor device 120 may be activated in a state in which a button or other equivalent input provided on the input unit 140 is pushed. In other words, the touch sensor device 120 may be activated only in a state in which the user touches the touch sensor device 120 while providing an input (e.g., pushing the button). As an example, to prevent or avoid one of the touch sensor units 120a to 120g from being activated, the input unit 140 may be provided with a mechanism which locks out a user from activating a touch sensor unit unless an input or button is depressed to "unlock" the touch sensor device, to thereby allow a user to activate the touch sensor device and/or one of the touch sensor units 120a to 120g.

FIG. 3 is a perspective view illustrating another embodiment of the X-ray imaging apparatus.

More specifically, as illustrated in FIGS. 1 to 3, the touch sensor device 120 may be located at a lateral side of the support member 110 on which the object is placed.

For example, the touch sensor device 120, as illustrated in FIGS. 1 and 2, may be located at an upper end or a lower end of the top plate. If the touch sensor device 120 is placed at the lower end of the top plate, the top plate may be formed of a material capable of transmitting touch by the user's finger or by the touch pen to allow the touch sensor device 120 to sense touch.

Additionally, as illustrated in FIG. 3, the touch sensor device 120 may be located at a lateral surface of the top plate defining the support member 110. In this case, the top plate may be formed of an X-ray permeable material to transmit X-rays to the detector 130 that is located at the lower end of the top plate.

FIGS. 4 to 7 are plan views illustrating different embodiments of the X-ray detection module.

As illustrated in FIGS. 4 to 7, the X-ray detection module 100 according to the embodiment of the present invention may include the touch sensor device 120 to sense an external touch and the X-ray detector 130 to detect X-rays.

The X-ray detector 130 may include an X-ray detection panel divided into a plurality of pixels. The respective pixels of the X-ray detection panel may include a scintillator that receives X-rays to output photons, a photodiode that receives the photons to change the photons into an electric signal, and a storage unit that stores the electric signal, for example, a storage capacitor.

The X-ray detector 130 may store X-rays received through the respective pixels of the X-ray detection panel as an electric signal to generate an X-ray image.

Figure 4:
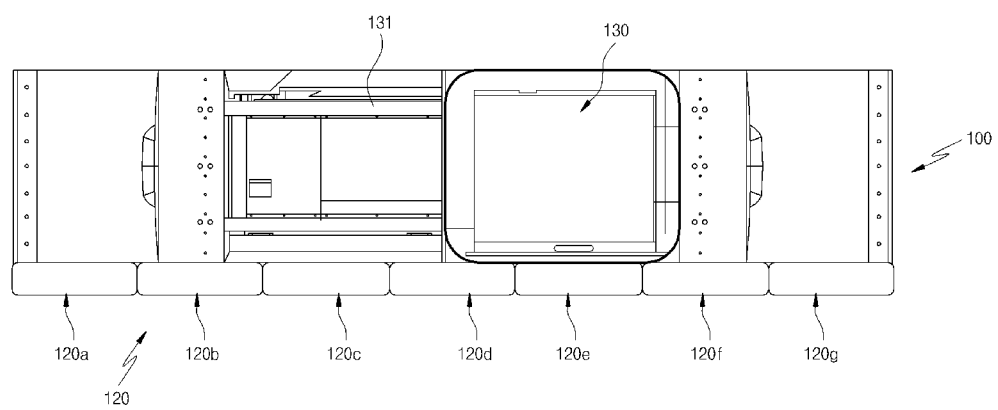
FIG. 4 is a plan view illustrating an embodiment of an X-ray detection module.
Figure 5:
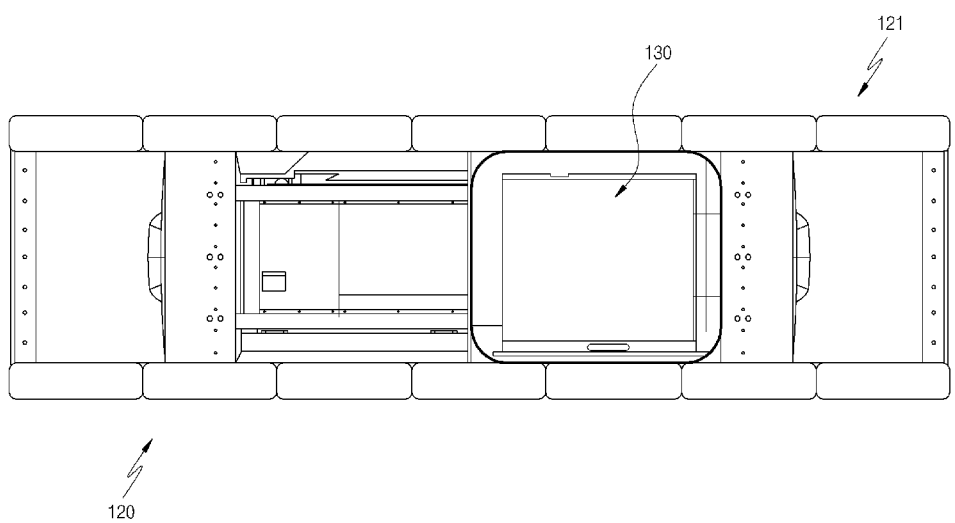
FIG. 5 is a plan view illustrating another embodiment of the X-ray detection module.

As illustrated in FIGS. 4 and 5, according to an embodiment of the present invention, the X-ray detector 130 is movable in at least one direction. For example, as illustrated in FIG. 4, the X-ray detector 130 may be moved in a particular direction or an opposite direction thereof along a guide rail 131 installed to a lower end of the X-ray detector 130. For example, the X-ray detector 130 may be moved back and forth, forward and backward, up and down, left and right, etc. For example, the X-ray detector 130 may be moved in a left-and-right direction as illustrated in FIG. 4.

The X-ray detector 130 may be moved, based on a position of the object, to a position where the X-ray detector 130 may receive X-rays having passed through the object. The X-ray detector 130 may preferably be moved, based on a position of the object, to a position where the X-ray detector 130 may best receive X-rays having passed through the object to thereby obtain a higher quality X-ray image.

According to an embodiment of the present invention, the touch sensor device 120 may include the plurality of sensor units 120a to 120g as illustrated in FIG. 4, and the plurality of touch sensor units 120a to 120g may be arranged at the lateral side of the X-ray detector 130 that detects X-rays from the X-ray irradiation module 200. In particular, according to an embodiment, the touch sensor units 120a to 120g may be arranged in a line in a movement direction of the X-ray detector 130.

According to another embodiment of the present invention, touch sensor devices 120 and 121 may be arranged near both boundaries of the detector 130 in a movement direction of the detector 130 as illustrated in FIG. 5. In other words, the plurality of touch sensor units 120a to 120g of the touch sensor device 120 may be arranged along a first line along a first boundary of the detector 130, and along a second line along a second boundary of the detector 130.

When the touch sensor devices 120 and 121 are arranged at both sides in the movement direction of the detector 130 as illustrated in FIG. 5, the user may control the X-ray imaging apparatus by touching any one of both lateral surfaces of the X-ray imaging apparatus illustrated in FIGS. 1 to 3. Therefore, improved convenience in touch action may be obtained as compared to the case in which the touch sensor device 120 is placed at one side in the movement direction of the detector 130 as illustrated in FIG. 4.

Figure 6:
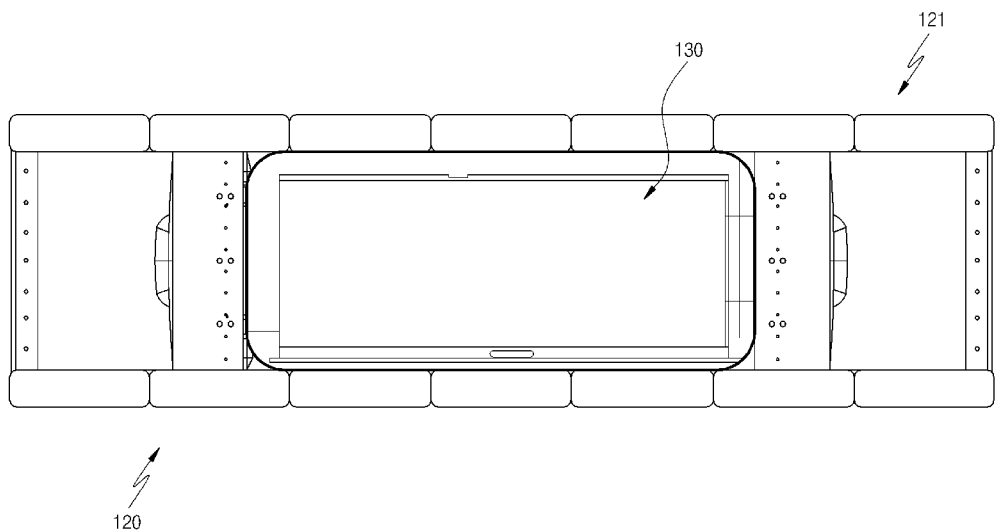
FIG. 6 is a plan view illustrating another embodiment of the X-ray detection module.

According to a further embodiment of the present invention, the X-ray detector 130 may be fixed as illustrated in FIG. 6.

In this case, the X-ray detector 130 may have a wider light receiving area than that of the movable X-ray detector 130, so as to more appropriately detect X-rays having passed through the object.

The touch sensor devices 120 and 121, as illustrated in FIG. 6, may be arranged at the lateral side of the fixed X-ray detector 130. According to an embodiment, as described above with reference to FIG. 4, the touch sensor devices 120 and 121 may be arranged only at one side of the X-ray detector 130. Also, according to another embodiment, as illustrated in FIG. 6, the touch sensor devices 120 and 121 may be arranged respectively at both sides of the X-ray detector 130.

Figure 7:
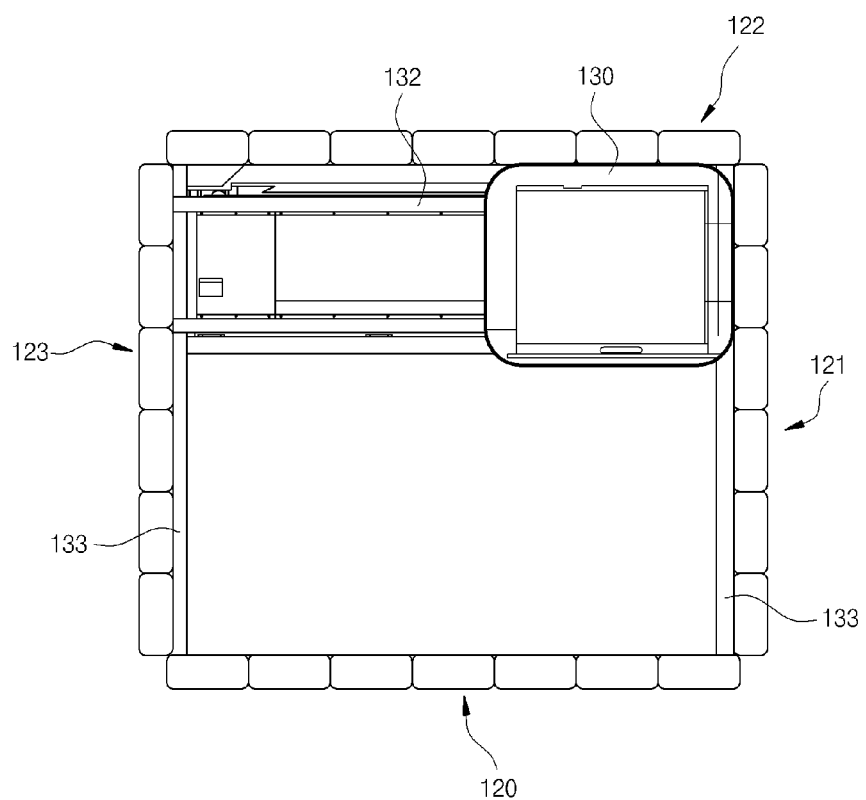
FIG. 7 is a plan view illustrating a further embodiment of the X-ray detection module.

According to a further embodiment of the present invention, the X-ray detector 130 may be moved in four directions as illustrated in FIG. 7.

In this case, the X-ray detection module 100 may include the X-ray detector 130, a first vertical or horizontal guide rail 132 or 133 located at the lower end of the X-ray detector 130 to vertically or horizontally guide the X-ray detector 130, and a second horizontal or vertical guide rail 133 or 132 extending perpendicular to the first guide rail 132 or 133 to vertically or horizontally guide the X-ray detector 130. That is, the X-ray detection module 100 may include the X-ray detector 130, a first guide rail to guide the X-ray detector 130 in a first direction, and a second guide rail to guide the X-ray detector 130 in a second direction. The first direction and second direction may be perpendicular to one another. The first guide rail and second guide rail may also be perpendicular to one another.

The X-ray detector 130 may be moved in four directions within a movement zone of the movable X-ray detector 130 along the first guide rail 132 or 133 or the second guide rail 133 or 132, and may stop at a particular position in a 2D plane.

In this case, touch sensor devices 120 to 123 may be arranged around a movement zone of the movable X-ray detector 130.

According to an embodiment of the present invention, similar to the above description of FIGS. 4 to 6, the touch sensor devices 120 to 123 may be arranged in the movement direction of the X-ray detector 130. Referring to FIG. 7, the first and third touch sensor devices 120 and 122 may be arranged in parallel to a horizontal movement direction of the X-ray detector 130, and similarly the second and fourth touch sensor devices 121 and 123 may be arranged in parallel to a vertical movement direction of the X-ray detector 130.

The X-ray imaging apparatus may further include a controller 300.

Figure 8:
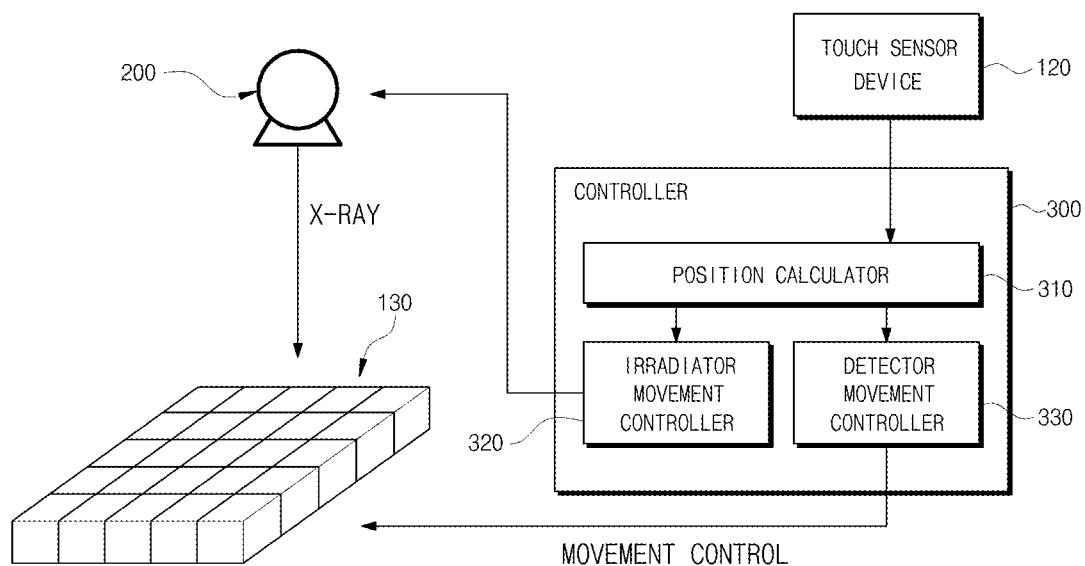
FIG. 8 is a view explaining a controller according to an embodiment of the X-ray imaging apparatus.

FIG. 8 is a view explaining a controller according to an embodiment of the X-ray imaging apparatus.

The controller 300 may be installed in an information processing apparatus connected to at least one of the X-ray irradiation module 200 and the X-ray detection module 100 via a wired or wireless communication network, or a combination thereof. The information processing apparatus which the controller 300 is installed within may be a work station, a personal computer, laptop, tablet and smartphone, etc. And the controller may be installed within the above-described X-ray detection module 100.

As illustrated in FIG. 8, according to an embodiment of the present invention, the controller 300 may include a position calculator 310, an irradiator movement controller 320, and a detector movement controller 330.

The position calculator 310 may calculate a coordinate value of at least one movement position of the X-ray irradiation module 200 and the X-ray detection module 100 based on a touch position sensed by the touch sensor device 120. That is, when any one of the plurality of touch sensor units 120a to 120g of the touch sensor device 120 is touched, or when a particular position of any one touch sensor unit of the plurality of touch sensor units 120a to 120g is touched, the position calculator 310 receives an electric signal generated from the touched one of the touch sensor units 120a to 120g or the touched particular position of any one of the touch sensor units 120a to 120g, and acquires a coordinate value of a position to which the X-ray irradiation module 200 and/or the X-ray detection module 100 will be moved based on the received electric signal.

Once the coordinate value of the movement position has been acquired by the position calculator 310, the coordinate value may be transmitted to at least one movement controller of the irradiator movement controller 320 and the detector movement controller 330. The at least one movement controller of the irradiator movement controller 320 and the detector movement controller 330 makes at least one controlling signal to control of the movement of at least one of the X-ray irradiation module 200 and the X-ray detector 130. And the at least one movement controller sends the at least one controlling signal to at least one driving unit of a driving unit of the X-ray irradiation module 200 and a driving unit of the X-ray detector 130. The driving units may move at least one of the X-ray irradiation module 200 and the X-ray detector 130 based on the at least one controlling signal. Thus at least one of the X-ray irradiation module 200 and the X-ray detector 130 may be moved based on the transmitted coordinate value.

In this case, if the X-ray detector 130 is fixed as illustrated in FIG. 6, the coordinate value of the movement position may be transmitted only to the irradiator movement controller 320, such that only the X-ray irradiation module 200 may be moved.

If the X-ray detector 130 is movable in a given direction as illustrated in FIGS. 4, 5 and 7, the coordinate value may be transmitted to the detector movement controller 330, to enable control of movement of the X-ray detector 130. In this case, similarly, the coordinate value may be transmitted to the irradiator movement controller 320, to allow the X-ray irradiation module 200 to be moved in response to movement of the detector 130.

According to an embodiment of the present invention, the controller 300 may acquire a coordinate value of a post-movement position only from a partial region of the touch sensor device 120 selected by the user or a predetermined partial region of the touch sensor device 120. For example, the controller 300 may acquire a coordinate value of a touch position of the touch sensor device 120 where the user previously selects using the input unit 140 as illustrated in FIG. 3, for example, of a touch position of a particular touch sensor unit (at least one of the touch sensor units 120a to 120g), without acquiring coordinate values of other touch positions. The input unit 140 may be embodied by, for example, an apparatus or device such as a keyboard, pedal or footswitch, mouse, touchscreen, graphical user interface, button, or voice control or microphone, or combinations thereof, to enable a user to provide an instruction via the input unit.

According to an embodiment of the present invention, the controller 300 may acquire a coordinate value of a touch position when the touch sensor device 120 is touched for a predetermined time or longer. In other words, if the user performs a touch action for a predetermined time or longer on a position, i.e. if the user continuously touches the touch position for a predetermined time or longer, the controller 300 may attempt to acquire a coordinate value of the user touch position.

Figure 9A:
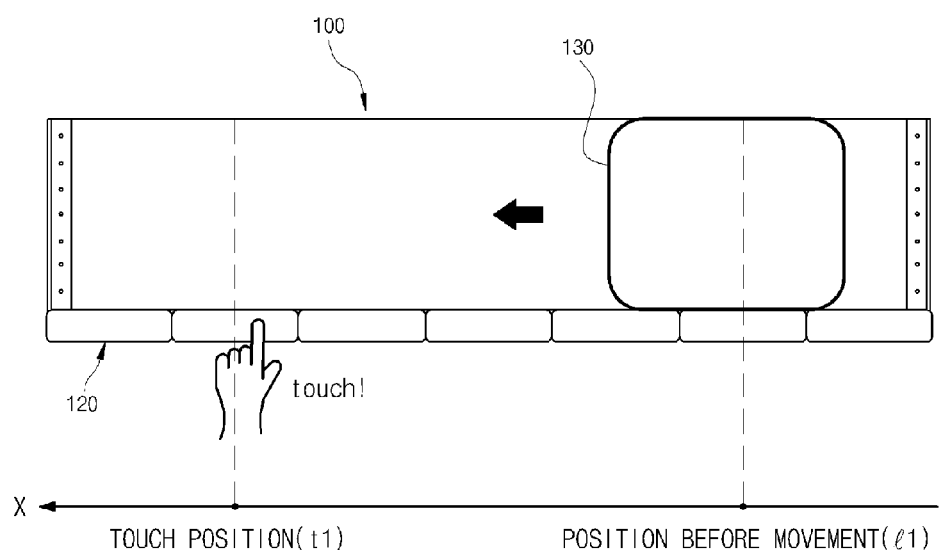
FIGS. 9A and 9B are views explaining an embodiment of operation of the X-ray detection module.
Figure 9B:
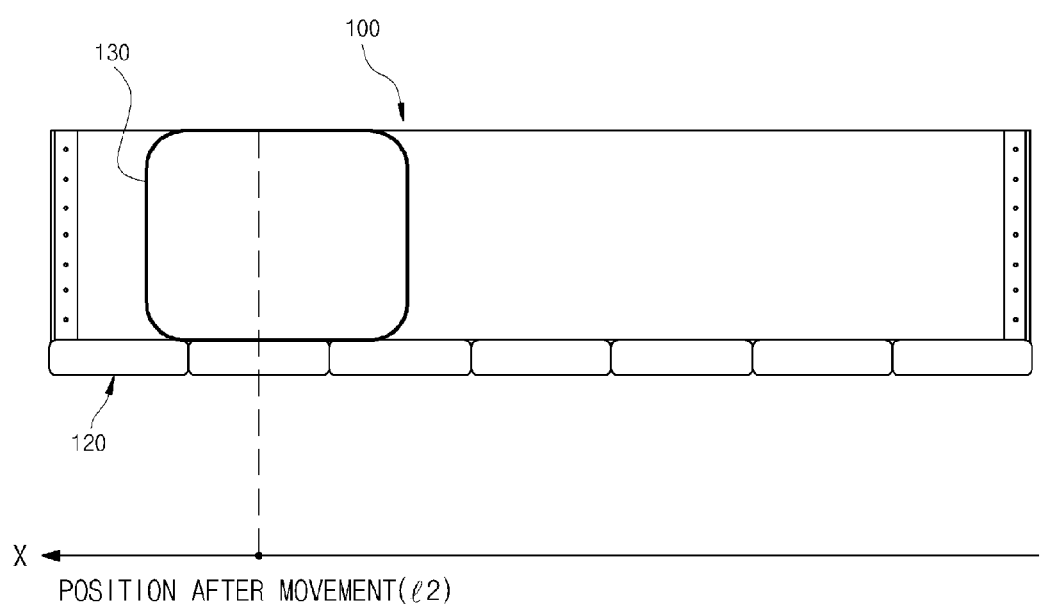

FIGS. 9A and 9B are views explaining an embodiment of operation of the X-ray detection module.

FIG. 9A illustrates an embodiment of the X-ray detection module 100 in which the touch sensor device 120 including the plurality of touch sensor units is disposed on a side in a movement direction of the X-ray detector 130.

The X-ray detector 130 of FIG. 9A may be movable in opposite directions on a single straight line.

As illustrated in FIG. 9A, the X-ray detector 130 is initially located at a predetermined point, i.e. a position before movement. Representing the position as any one point of a 1-Dimensional (1D) coordinate system, the position may be designated by a point I1 on the X-axis.

Thereafter, the user touches any one point of the touch sensor device 120 as illustrated in FIG. 9A.

Then, the above-described controller 300 calculates a coordinate value corresponding to any one touched point, for example, a 1D coordinate value. As a result, a coordinate value of a touch position corresponding to any one touched point, i.e. a 1D coordinate value on the X-axis t1 is acquired.

Then, the controller 300, in particular, the detector movement controller 330 moves the X-ray detector 130, based on the acquired coordinate value, to a post-movement position, i.e. a point I2 on the X-axis.

As a result, movement of the X-ray detector 130 in response to the user touch action on the touch sensor device 120 may be controlled.

According to an embodiment of the present invention, the X-axis coordinate value I2 of the post movement position may be equal to the X-axis coordinate value t1 of the touch position, but may not be essentially equal thereto. In other words, the post movement position of the X-ray detector 130 may be a position corrected based on predetermined criteria with respect to the touch position. For example, the X-axis coordinate value I2 may be acquired by calculating the X-axis coordinate value t1 based on predetermined criteria. For example, the coordinate value I2 may be acquired by adding or subtracting a constant to or from the X-axis coordinate value t1. Here, as shown in FIG. 9A, the user's touch may be slightly offset from the coordinate value t1 determined by the controller 300. The coordinate value t1 may be determined as a midpoint or center position along the X-axis of the touch sensor unit which is activated by the user, for example, as shown in FIG. 9A. For example, each touch sensor unit may have a known or predefined length.

The position of the X-ray detector 130 may be referenced with respect to a center of the X-ray detector 130, as shown in FIG. 9B, for example. Alternatively, the position of the X-ray detector 130 may be referenced with respect to the leading edge of the X-ray detector 130 (i.e., the side of the X-ray detector 130 which corresponds to the movement direction), or may be referenced with respect to the trailing edge of the X-ray detector 130 (i.e., the side of the X-ray detector 130 which is opposite to the movement direction). The position of the X-ray irradiator 200 may similarly be determined according to various reference points.

Accordingly, as necessary, it may be possible to increase or decrease a movement distance of the X-ray detector 130 as compared to the user touch position.

This may equally be applied to the case in which the touch sensor device 120 is arranged in the form of a square surrounding an X-ray detector movement zone as illustrated in FIG. 7. In this case, for movement in a plane, the touch position may be represented by a 2D coordinate system defined by an X-axis and a Y-axis.

According to another embodiment of the present invention, instead of the X-ray detector 130, the X-ray irradiation module 200 may be controlled so as to be moved to the post movement position corresponding to the coordinate value I2. According to a further embodiment of the present invention, both the X-ray detector 130 and the X-ray irradiation module 200 may be controlled so as to be moved to the post movement position corresponding to the coordinate value I2.

Figure 10:
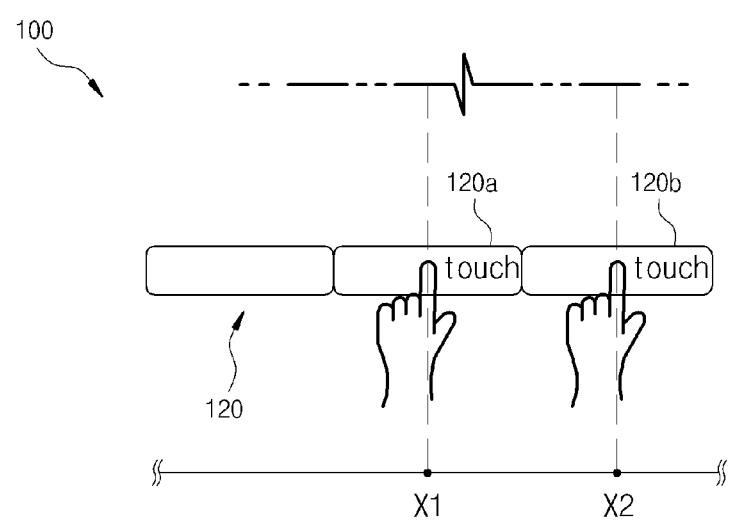
FIG. 10 is a view explaining an embodiment of touch operation of the X-ray detection module.
Figure 11:
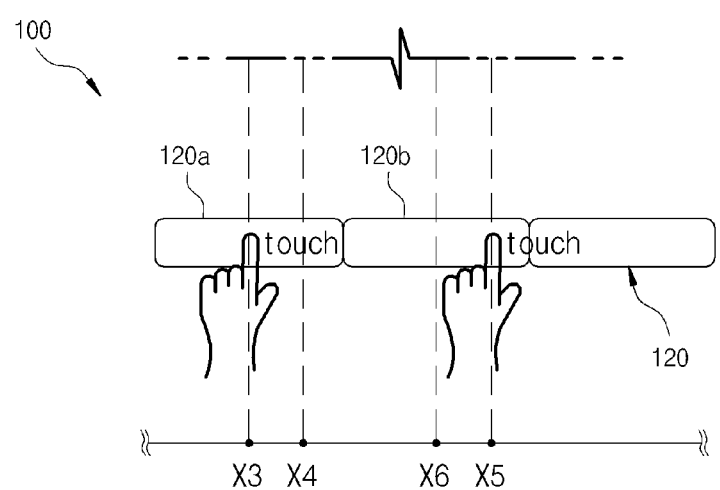
FIG. 11 is a view explaining another embodiment of touch operation of the X-ray detection module.

FIGS. 10 and 11 are views explaining various embodiments of a touch action of the X-ray detection module.

As illustrated in FIG. 10, according to an embodiment of the present invention, a position where the user touches using the finger or the touch pen may be recognized as a touch position.

In other words, if the user touches a particular point of the touch sensor unit 120a, the touched point may be recognized as a touch position, and thus the controller 300 may acquire an X-axis coordinate value x1 of the touched point. Similarly, when a touch action is performed on another touch sensor unit 120b, the controller 300 may acquire an X-axis coordinate value x2 of the touched point.

Thereafter, the X-ray detector 130 may be moved to a post-movement position based on the coordinate value x1 or x2 as described above.

According to another embodiment of the present invention, as illustrated in FIG. 11, instead of a position on which a touch action is performed, another position may be recognized as a touch position.

For example, even if the user performs a touch action on a point of any one touch sensor unit 120a corresponding to a coordinate value x3, another point, for example, a middle point of the same touch sensor unit 120a (a point designated by a coordinate value x4) may be recognized as a touch position. That is, as shown in FIG. 11, when a user touches a middle point of the touch sensor unit, a point between an end of the touch sensor unit and the touch may be determined as the touch position by the controller 300. For example, the touch position may be determined as a midpoint between a position where the user touches the touch sensor unit and a closest end of the touch sensor unit.

Similarly, even in the case of another touch sensor unit 120b, rather than a point on which a touch action is performed (a point designated by a coordinate value x5), a middle point of the same touch sensor unit 120b (a point designated by a coordinate value x6) may be recognized as a touch position.

In this case, the controller 300 may recognize the points corresponding to the coordinate values x4 and x6, rather than the points corresponding to the coordinate values x3 and x5 where the touch action is performed, as touch positions, and may calculate a post-movement position of the X-ray detector 130 and/or the X-ray irradiation module 200, thereby controlling movement of the X-ray detector 130 and/or the X-ray irradiation module based on the calculated result. The controller 300 may determine touch positions according to the above-described embodiments based upon a user input which may control how one or more of the touch sensor units determines a touch position.

According to an embodiment of the present invention, movement of the X-ray irradiation module 200 and/or the X-ray detector 130 may be controlled so as to be performed only while the touch sensor device 120 senses touch. In other words, the X-ray irradiation module 200 or the X-ray detector 130 may be moved only while the user touches the touch sensor device 120. If the user separates the finger from the touch sensor device 120 to stop a touch action, movement of the X-ray irradiation module 200 or the X-ray detector 130 may stop.

Figure 12:
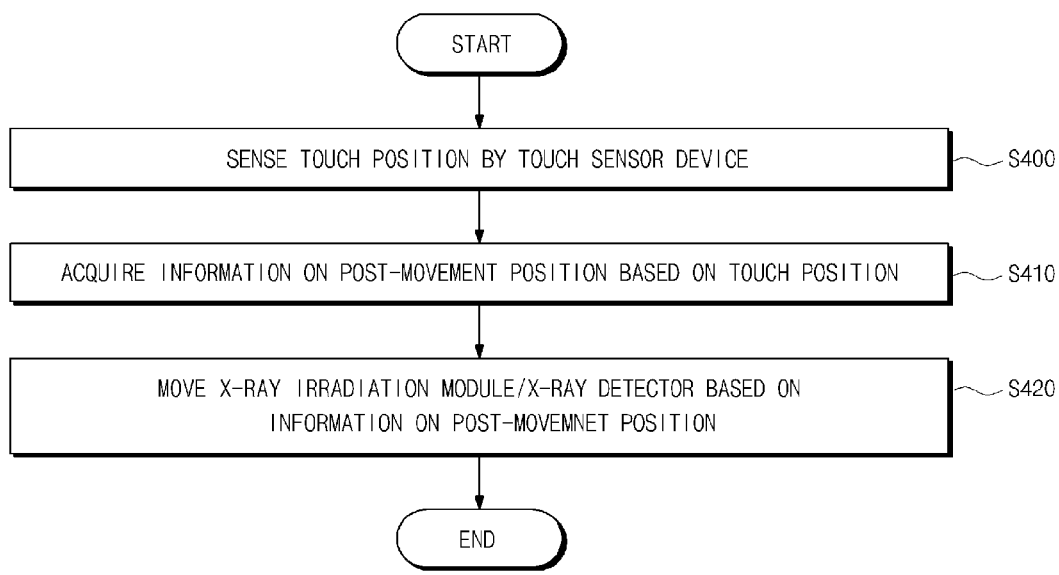
FIG. 12 is a flowchart illustrating a control method of the X-ray imaging apparatus.

FIG. 12 is a flowchart illustrating a control method of the X-ray imaging apparatus.

As illustrated in FIG. 12, with the control method of the X-ray imaging apparatus according to the embodiment of the present invention, the touch sensor device 120 placed at the lateral side of the X-ray detector 130 or in a movement direction of the X-ray detector 130 senses a user touch action at a position on the touch sensor device 120 (S400).

Next, positional information on movement positions of the X-ray irradiation module 200 and the X-ray detector 130, i.e., a coordinate value of a post-movement position may be acquired based on the sensed touch position (S410). This operation may be performed by the controller 300.

Next, in response to a control instruction of the controller 300 based on the positional information on the post-movement position, the X-ray irradiation module 200 and/or the X-ray detector 130 may be simultaneously or sequentially moved to reach the post-movement position (S420).

Figure 13:
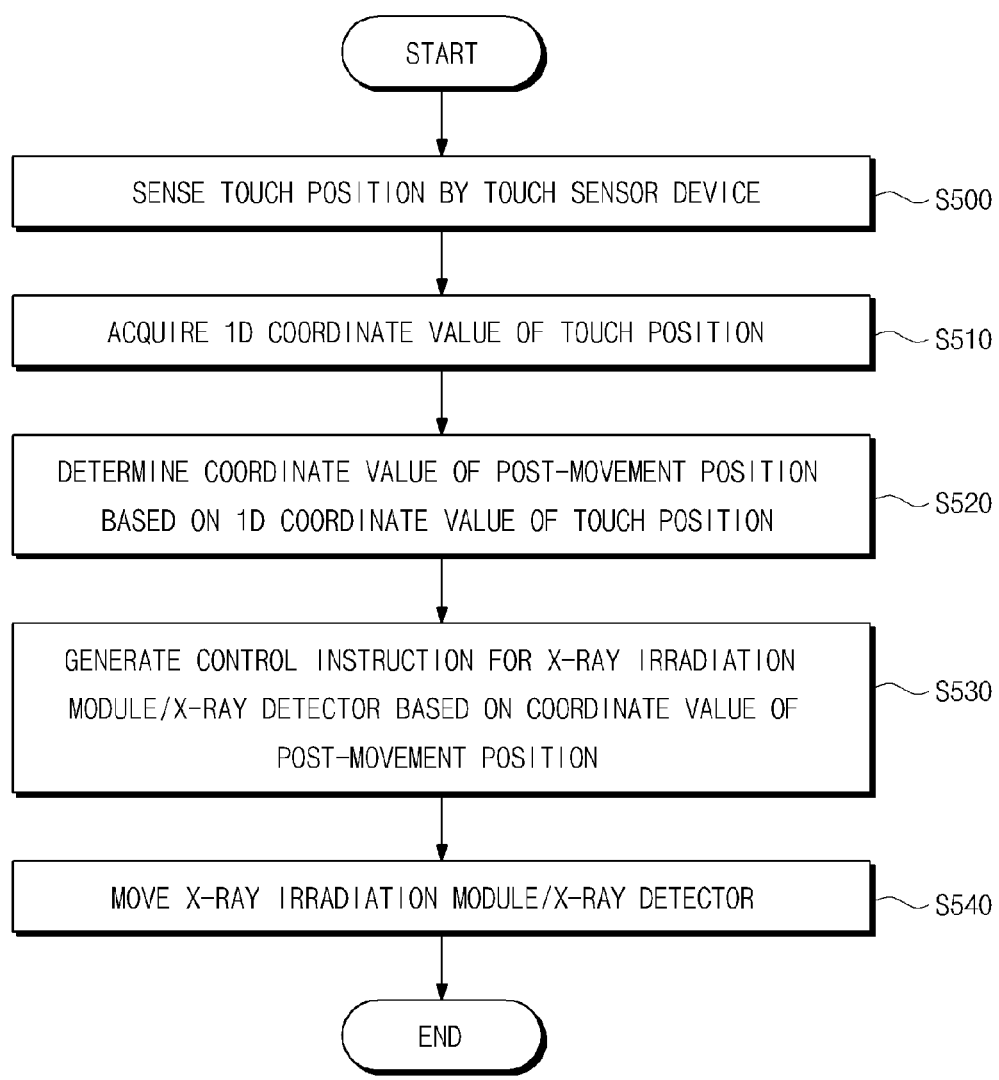
FIG. 13 is a flowchart illustrating an embodiment of the control method of the X-ray imaging apparatus.

FIG. 13 is a flowchart illustrating an embodiment of the control method of the X-ray imaging apparatus.

As illustrated in FIG. 13, according to an embodiment of the control method of the X-ray imaging apparatus, the touch sensor device 120 of the X-ray imaging apparatus senses a user touch action at a position thereon (S500).

Then, an electric signal corresponding to the user touch action is generated and transmitted to the controller 300. The controller 300 acquires a 1D coordinate value of a touch position (S510). For example, the 1D coordinate may be touched by the user may correspond to coordinate values t1, x1, x2, x3, or X5 as shown in FIG. 9A, FIG. 10, and FIG. 11. In an embodiment, a short-distance point from the touch position may be recognized as the touch position. For example, as illustrated in FIG. 11, a point touched by the user corresponding to a coordinate value x3 may be shifted by a predetermined amount to a point corresponding to the coordinate value x4, and the coordinate value x4 may be recognized as the touch position. For example, as illustrated in FIG. 11, a point touched by the user corresponding to a coordinate value x5 may be shifted by a predetermined amount to a point corresponding to the coordinate value x6, and the coordinate value x6 may be recognized as the touch position. Alternatively, as illustrated in FIG. 10, a point touched by the user corresponding to a coordinate value x1 may be recognized as the touch position and a point touched by the user corresponding to a coordinate value x2 may be recognized as the touch position. That is, the recognized touch position equals or coincides with the point touched by user.

Next, the controller 300 determines a coordinate value of a desired post-movement position based on the 1D coordinate value of the touch position (S520). According to embodiments, the coordinate value of the post-movement position may be equal to or differ from the coordinate value of the touch position.

The controller 300 generates a control instruction for at least one of the X-ray irradiation module 200 and the X-ray detector 130 based on the coordinate value of the post-movement position (S530), and transmits the control instruction to at least one of the X-ray irradiation module 200 and the X-ray detector 130.

The at least one of the X-ray irradiation module 200 and the X-ray detector 130 may be moved to a post-movement position I2 from position I1 as illustrated in FIGS. 9A and 9B in response to the control instruction (S540).

Figure 14:
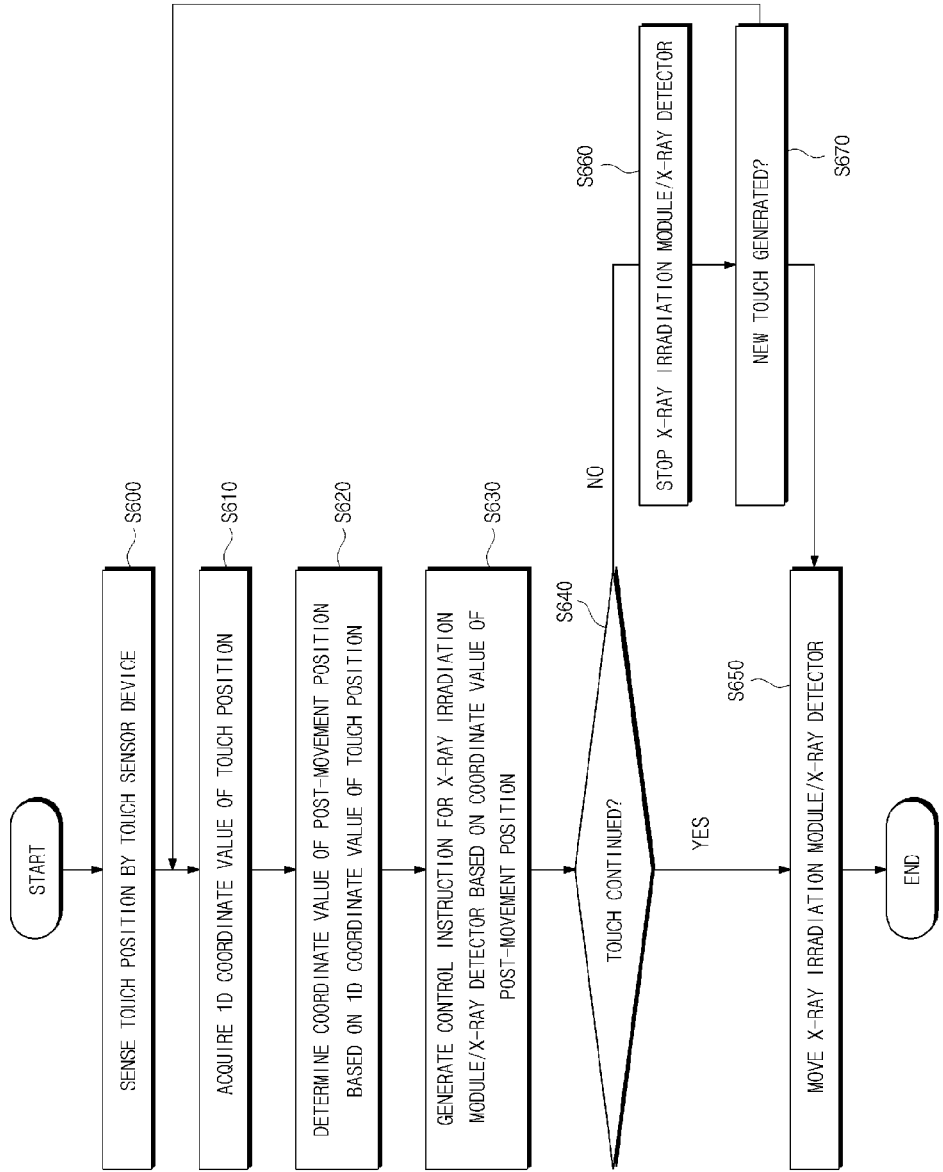
FIG. 14 is a flowchart illustrating another embodiment of the control method of the X-ray imaging apparatus.

FIG. 14 is a flowchart illustrating another embodiment of the control method of the X-ray imaging apparatus.

As illustrated in FIG. 14, according to another embodiment of the control method of the X-ray imaging apparatus, first, the touch sensor device 120 of the X-ray imaging apparatus senses a user touch action at a position thereon (S600).

Then, the controller 300 acquires a 1D coordinate value of a sensed touch position (for example, x1 to x6 of FIGS. 10 and 11) (S610), and determines a coordinate value of a post-movement position of the X-ray irradiation module 200 and/or the X-ray detector 130 based on the 1D coordinate value of the touch position (S620).

A control instruction for at least one of the X-ray irradiation module 200 and the X-ray detector 130 is generated based on the coordinate value of the post-movement position (S630).

In this case, if the user continuously touches the touch sensor device 120 (S640), at least one of the X-ray irradiation module 200 and the X-ray detector 130 is moved based on the generated control instruction (S650).

If the user stops the touch action on the touch sensor device 120, in other words, if the user separates the finger or the touch pen from the touch sensor device 120, movement of the X-ray irradiation module 200 and/or the X-ray detector 130 stops (S660).

Thereafter, if a new touch action is sensed as the user again touches the touch sensor device 120 (S670), a new post-movement position, for example, a 1D coordinate value is calculated based on the sensed touch position. These operations are repeated.

Accordingly, the X-ray irradiation module 200 and the X-ray detector 130 may be moved only while the user continuously performs a touch action. That is, as the X-ray irradiation module 200 and the X-ray detector 130 are movable only while the user continuously touches the touch sensor device 120, movement of the X-ray irradiation module 200 and the X-ray detector 130 may be more conveniently controlled.

Figure 15:
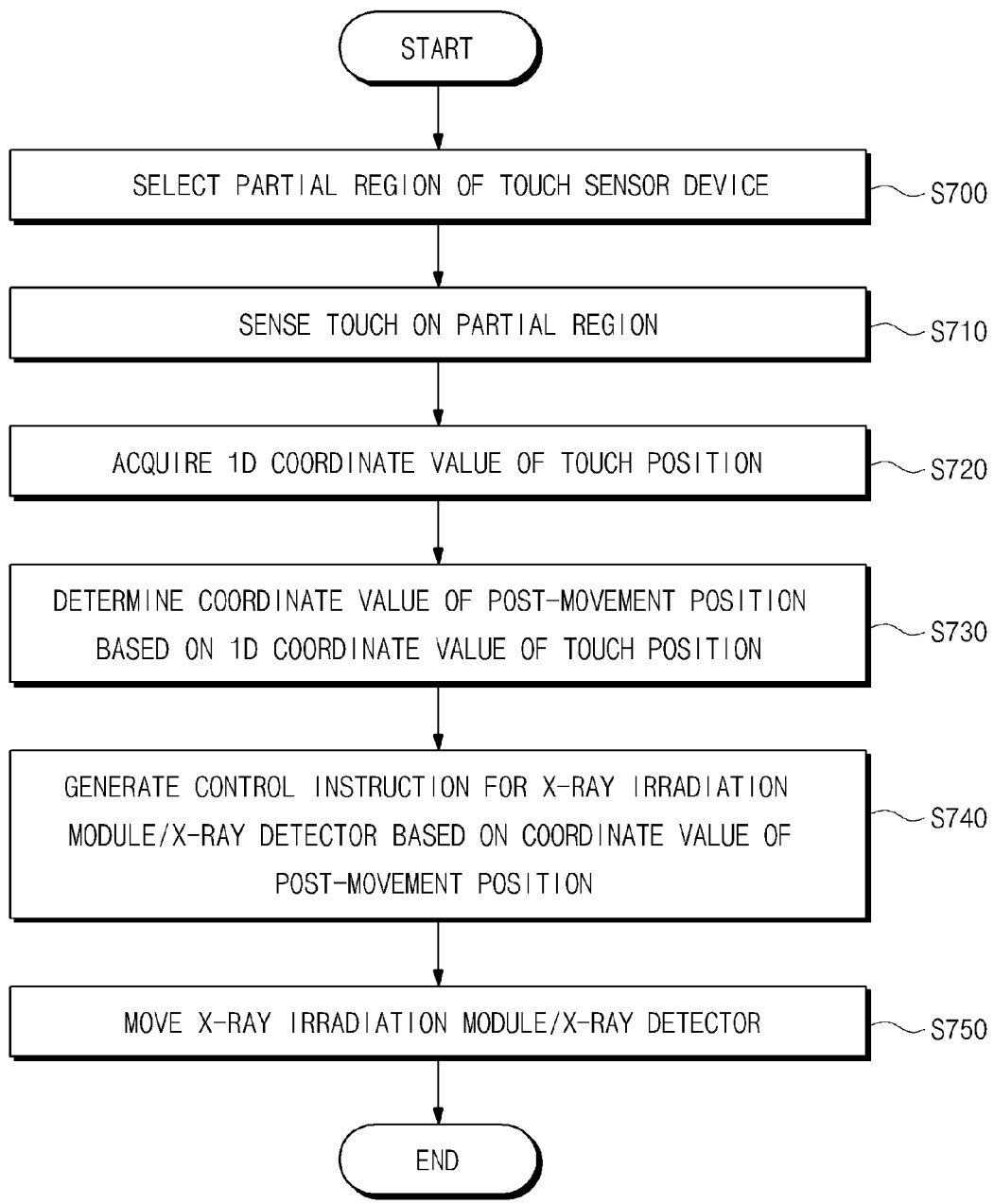
FIG. 15 is a flowchart illustrating a further embodiment of the control method of the X-ray imaging apparatus.

FIG. 15 is a flowchart illustrating a further embodiment of the control method of the X-ray imaging apparatus.

As illustrated in FIG. 15, to control the X-ray imaging apparatus, first, a partial region of the touch sensor device 120 is selected (S700). According to an embodiment, the partial region may be selected via the input unit 140. Then, the touch sensor device 120 senses a touch action on the selected partial region thereof (S710). According to another embodiment, if the user continuously touches a particular region for a predetermined time or longer, the particular region may be selected as the aforementioned partial region. In this case, the selection of the partial region (S700) and the sensing of touch on the particular region (S710) may be performed simultaneously.

Then, the controller 300 acquires a coordinate value of a touch position, for example, a 1D coordinate value (S720), and determines a coordinate value of a desired movement position of at least one of the X-ray irradiation module 200 and the X-ray detector 130 based on the coordinate value of the touch position, for example, based on the 1D coordinate value (S730). Next, the controller 300 generates a control instruction for at least one of the X-ray irradiation module 200 and the X-ray detector 130 based on the coordinate value of the post-movement position (S740).

At least one of the X-ray irradiation module 200 and the X-ray detector 130 is moved in response to the generated control instruction (S750).

As is apparent from the above description, the controller 300 determines a coordinate value of a desired post-movement position based on the 1D coordinate value of the touch position. In an embodiment in which the X-ray detector 130 moves in four directions as illustrated in FIG. 7, the controller may first determine a coordinate value of a desired post-movement position based on a first 1D coordinate value of a first touch position (for example, in one of the horizontal or vertical directions). Then, the controller may next determine a coordinate value of a desired post-movement position based on a second 1D coordinate value of a second touch position (for example, in the other of the horizontal or vertical directions). In an embodiment, the X-ray irradiation module 200 and/or the X-ray detector 130 may only be moved after both the first and second 1D coordinate values are determined. Alternatively, the X-ray irradiation module 200 and/or the X-ray detector 130 may sequentially be moved after each of the first and second 1D coordinate values are determined.

As is apparent from the above description, with an X-ray detection module, an X-ray imaging apparatus, and a control method of an X-ray imaging apparatus according to the embodiments of the present invention as described above, the user may easily and accurately move an X-ray irradiation module and/or an X-ray detector to a position where a user desires.

Thereby, it may be possible to prevent the user from inconveniently directly moving the X-ray irradiation module or the X-ray detector.

Further, a position of the X-ray irradiation module or the X-ray detector may be intuitively determined via a single touch action or a small number of simple touch actions, which may improve user convenience and reduce the entire X-ray imagining time.

Furthermore, as a result of moving the X-ray irradiation module and/or the X-ray detector to an accurate position, it may be possible to reduce the frequency of re-imaging, which may allow an object, for example, the patient to be exposed to less radiation.

Through use of the X-ray detection module, the X-ray imaging apparatus, and the control method of the X-ray imaging apparatus, it may be possible to prevent malfunction of a touch sensor device due to unintentional movement of the object, for example, of the patient during X-ray imaging.

Here it is noted that the X-ray detection module, X-ray imaging apparatus and control methods according to the example embodiments disclosed herein may be applied to a target object including a human, an animal, or to any other objects for which a X-ray imaging may be applied (e.g., security applications such as airport security or border security, industrial applications such as taking x-ray images of welds, art applications such as taking x-ray images of paintings, etc.).

The X-ray detection module, X-ray imaging apparatus and control methods according to the example embodiments disclosed herein may use one or more processors, which may include a microprocessor, central processing unit (CPU), digital signal processor (DSP), or application-specific integrated circuit (ASIC), as well as portions or combinations of these and other processing devices.

Each block of the flowchart illustrations may represent a unit, module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Methods for controlling an X-ray detection module and/or X-ray imaging apparatus according to the example embodiments disclosed herein may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules that are recorded, stored, or fixed in one or more computer-readable storage media, in order to perform the operations of the above-described embodiments, or vice versa. The program instructions may be executed by one or more processors. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although the embodiments of the present invention have been shown and described, it would be appreciated by those skilled in the art that changes may be made to these embodiments without departing from the principles and spirit of the invention, the scope of which is defined in the claims and their equivalents.

What is claimed is:
1. An X-ray imaging apparatus, comprising:
a support member configured to support an object to which X-rays are emitted;
a movable X-ray irradiator configured to emit the X-rays;
a movable X-ray detector configured to detect the X-rays emitted by the movable X-ray irradiator and movably installed to the support member;
a first touch sensor device, installed in at least one row along a first side of the support member, configured to sense a touch input;
a second touch sensor device, installed along a second side of the support member, configured to sense a touch input, the first side and the second side being perpendicular to one another; and
a controller configured to receive information, from at least one of the first touch sensor device and the second touch sensor device, of at least one position to which at least one of the X-ray irradiator and the X-ray detector is to be moved, and to control at least one of the X-ray irradiator and the X-ray detector to be moved based on the information of the at least one position to which the at least one of the X-ray irradiator and the X-ray detector is to be moved.

2. The X-ray imaging apparatus according to claim 1, wherein the first touch sensor device is located at an outer periphery of the first side of the support member in a movement direction of the X-ray detector, and at an outer periphery of a third side of the support member in the movement direction of the X-ray detector, the first side and the third side being on opposite sides of the support member.

3. The X-ray imaging apparatus according to claim 1, wherein the at least one of the X-ray irradiator and the X-ray detector is moved while at least one of the first touch sensor device and the second touch sensor device senses the touch input.

4. The X-ray imaging apparatus according to claim 1, wherein at least one of the first touch sensor device and the second touch sensor device comprises a plurality of touch sensor units, and at least one of the plurality of touch sensor units are only able to be activated to sense the touch input.

5. The X-ray imaging apparatus according to claim 4, wherein a partial region of at least one of the first touch sensor device and the second touch sensor device is configured to be selected upon receiving a selection instruction via a separate input unit.

6. The X-ray imaging apparatus according to claim 3, wherein the at least one of the X-ray irradiator and the X-ray detector stops moving in response to failing to sense the touch input.

7. An X-ray detection table, comprising:
a movable X-ray detector configured to detect X-rays;
a touch sensor device configured to sense a touch input, the touch sensor device including a first plurality of touch sensor devices arranged in at least one row along a movement direction of the X-ray detector along a first side of the support member and a second plurality of touch sensor devices arranged along a second side of the support member, the first side and second side being perpendicular to one another,
wherein at least one of an X-ray irradiator and the X-ray detector is moved to a position where the touch input is sensed by the touch sensor device after the touch sensor device is continuously touched for a time greater than a predetermined threshold.

8. A control method of an X-ray imaging apparatus, the control method comprising:
sensing a touch input regarding at least one position to which at least one of the X-ray irradiator and the X-ray detector is to be moved, by a first touch sensor portion and a second touch sensor portion among a plurality of touch sensor portions of a touch sensor device;
acquiring positional information on a movement position of at least one of a X-ray irradiator and a X-ray detector based on the touch input sensed by the touch sensor device; and
moving the at least one of the X-ray irradiator and the X-ray detector based on the positional information after the touch sensor device is continuously touched for a time greater than a predetermined threshold,
wherein the first touch sensor portion is installed to a first side of the support member in at least one row along a movement direction of an X-ray detector and the second touch sensor portion is installed to a second side of the support member, and wherein the first side and second side are perpendicular to one another.

9. The control method according to claim 8, wherein the sensing of the touch input by the touch sensor device comprises sensing a touch input by at least one touch sensing device of a plurality of touch sensing devices arranged at an outer periphery of a first side of the support member in the movement direction of the X-ray detector, and at an outer periphery of a second side of the support member in the movement direction of the X-ray detector, the first side and the second side being on opposite sides of the support member.

10. The control method according to claim 8, wherein the movement of the at least one of the X-ray irradiation module and the X-ray detector comprises moving at least one of the X-ray irradiator and the X-ray detector during the sensing of the touch input.

11. An X-ray imaging apparatus, comprising:
a support member configured to support an object to which X-rays are emitted;
an X-ray irradiator configured to emit the X-rays;
an X-ray detector configured to detect X-rays from the X-ray irradiator, and movably installed to the support member;
a first plurality of touch sensor devices to sense a touch input, installed in at least one row along a first side of the support member;
a second plurality of touch sensor devices to sense a touch input, installed along a second side of the support member, the first side and second side are perpendicular to one another; and
a controller configured:
to receive information, from at least one of the first plurality of touch sensor devices and the second plurality of touch sensor devices, of at least one position to which at least one of the X-ray irradiator and the X-ray detector is to be moved,
to determine a first coordinate value corresponding to a position of a first sensed touch input at one of the first plurality of touch sensor devices and the second plurality of touch sensor devices, and
to calculate a post-movement coordinate value to which at least one of the X-ray irradiator and the X-ray detector is to be moved.

12. The X-ray imaging apparatus according to claim 11, wherein the X-ray detector moves in a direction parallel to the first side when a touch input is sensed at one of the first plurality of touch sensor devices, and moves in a direction parallel to the second side when a touch input is sensed at one of the second plurality of touch sensor devices.

13. The X-ray imaging apparatus according to claim 11, wherein each of the first plurality of touch sensor devices are selectively activated or deactivated according to a user input.

14. The X-ray imaging apparatus according to claim 11, wherein the first coordinate value of the first sensed touch input is substantially equal to the post-movement coordinate value.

15. The X-ray imaging apparatus according to claim 11, wherein the first coordinate value of the first sensed touch input is corrected and the post-movement coordinate value is offset from the first coordinate value by a predetermined amount.

* * * * *